United States Patent
Samain et al.

(10) Patent No.: US 10,477,938 B2
(45) Date of Patent: Nov. 19, 2019

(54) MAKEUP DEVICE COMPRISING A PLURALITY OF COSMETIC DYES

(71) Applicant: L'OREAL, Paris (FR)

(72) Inventors: Henri Samain, Bievres (FR); Franck Giron, Paris (FR)

(73) Assignee: L'OREAL, Paris (FR)

(*) Notice: Subject to any disclaimer, the term of this patent is extended or adjusted under 35 U.S.C. 154(b) by 577 days.

(21) Appl. No.: 15/108,294

(22) PCT Filed: Dec. 19, 2014

(86) PCT No.: PCT/IB2014/067138
§ 371 (c)(1),
(2) Date: Jun. 25, 2016

(87) PCT Pub. No.: WO2015/097620
PCT Pub. Date: Jul. 2, 2015

(65) Prior Publication Data
US 2016/0316886 A1 Nov. 3, 2016

(30) Foreign Application Priority Data
Dec. 27, 2013 (FR) ..................... 13 63637

(51) Int. Cl.
*B41J 3/407* (2006.01)
*A45D 33/00* (2006.01)
(Continued)

(52) U.S. Cl.
CPC .......... *A45D 33/00* (2013.01); *A45D 34/042* (2013.01); *A45D 40/30* (2013.01); *A45D 44/005* (2013.01);
(Continued)

(58) Field of Classification Search
CPC .... A45D 44/002; A45D 44/005; A45D 40/30; A45D 2200/25; B41J 3/407; A61Q 1/02;
(Continued)

(56) References Cited

U.S. PATENT DOCUMENTS

| 2,746,460 A | 5/1956 | Jellinek |
| 4,137,180 A | 1/1979 | Naik et al. |

(Continued)

FOREIGN PATENT DOCUMENTS

| CN | 1476319 A | 2/2004 |
| CN | 1519278 A | 8/2004 |

(Continued)

OTHER PUBLICATIONS

Office Action dated Apr. 23, 2018 in European Patent Application No. 14 833 256.2.
(Continued)

*Primary Examiner* — Huan H Tran
(74) *Attorney, Agent, or Firm* — Shumaker, Loop & Kendrick, LLP

(57) ABSTRACT

The invention relates to a makeup device comprising a substrate defining a printing surface having at least one region printed with at least one coloring dye layer to be applied onto human keratinous material. The at least one coloring dye has been deposited, via printing, onto the printing surface by at least one printer, particularly a digital printer; is not covered by an adhesive; and produces after application onto the keratinous material, at least one visible optical effect, namely color and/or sheen.

22 Claims, 4 Drawing Sheets

(51) Int. Cl.
  *A45D 44/00* (2006.01)
  *A45D 34/04* (2006.01)
  *A45D 40/30* (2006.01)
  *A61K 8/02* (2006.01)
  *A61K 8/46* (2006.01)
  *A61K 8/49* (2006.01)
  *A61K 8/60* (2006.01)
  *A61Q 1/02* (2006.01)

(52) U.S. Cl.
  CPC .............. *A61K 8/022* (2013.01); *A61K 8/466* (2013.01); *A61K 8/49* (2013.01); *A61K 8/602* (2013.01); *A61Q 1/02* (2013.01); *B41J 3/407* (2013.01); *A45D 2044/007* (2013.01); *A61K 2800/432* (2013.01); *A61K 2800/87* (2013.01)

(58) Field of Classification Search
  CPC ........ A61Q 19/00; A61Q 19/08; A61Q 19/02; A61Q 1/025; A61Q 9/04; A61Q 19/007; A61Q 19/06; A61Q 7/02; A61Q 1/04; A61Q 1/06
  See application file for complete search history.

(56) References Cited

U.S. PATENT DOCUMENTS

| | | |
|---|---|---|
| 4,804,719 A | 2/1989 | Weaver et al. |
| 4,874,554 A | 10/1989 | Lange et al. |
| 4,925,667 A | 5/1990 | Fellows et al. |
| 4,999,418 A | 3/1991 | Krutak et al. |
| 5,030,708 A | 7/1991 | Krutak et al. |
| 5,032,670 A | 7/1991 | Parham et al. |
| 5,043,376 A | 8/1991 | Sharma et al. |
| 5,047,084 A | 9/1991 | Miller et al. |
| 5,078,160 A * | 1/1992 | Carbonnier ............ A45D 40/00 132/320 |
| 5,102,980 A | 4/1992 | Krutak et al. |
| 5,104,913 A | 4/1992 | Sharma et al. |
| 5,106,942 A | 4/1992 | Krutak et al. |
| 5,194,463 A | 3/1993 | Krutak et al. |
| 5,281,659 A | 1/1994 | Weaver et al. |
| 5,913,315 A | 6/1999 | Todd |
| 5,958,560 A | 9/1999 | Ewan |
| 5,997,134 A | 12/1999 | Hotomi et al. |
| 5,997,136 A | 12/1999 | Fujisawa et al. |
| 6,013,248 A | 1/2000 | Luebbe et al. |
| 6,106,852 A | 8/2000 | Vineberg |
| 6,168,656 B1 | 1/2001 | Schulz et al. |
| 6,190,730 B1 | 2/2001 | Matsos et al. |
| 6,299,967 B1 | 10/2001 | Collins et al. |
| 6,312,124 B1 | 11/2001 | Desormeaux |
| 6,342,094 B1 | 1/2002 | Kabalnov |
| 6,367,484 B1 | 4/2002 | Ramin et al. |
| 6,428,164 B1 | 8/2002 | Missell et al. |
| 6,543,893 B2 | 4/2003 | Desormeaux |
| 6,622,733 B2 | 9/2003 | Saksa |
| 6,626,183 B1 | 9/2003 | Pietrocola |
| 7,241,503 B2 | 7/2007 | Noguchi |
| 8,007,062 B2 | 8/2011 | Edgar et al. |
| 8,083,422 B1 | 12/2011 | Simmons |
| 8,545,613 B2 * | 10/2013 | Blette .................. A61K 8/345 106/31.03 |
| 8,695,610 B2 | 4/2014 | Samain |
| 9,616,668 B1 | 4/2017 | Rabe |
| 2002/0020422 A1 | 2/2002 | Iosilevich |
| 2002/0061321 A1 | 5/2002 | Bara |
| 2002/0110672 A1 | 8/2002 | Muratore-Pallatino et al. |
| 2002/0155069 A1 | 10/2002 | Pruche |
| 2002/0164295 A1 | 11/2002 | Scavone et al. |
| 2003/0053976 A1 | 3/2003 | Tournilhac et al. |
| 2004/0057742 A1 | 3/2004 | Richtsmeier |
| 2004/0078278 A1 | 4/2004 | Dauga |
| 2004/0241423 A1 | 12/2004 | Ramin et al. |
| 2005/0148908 A1 | 7/2005 | Stover |
| 2006/0093943 A1 | 5/2006 | Hyo et al. |
| 2006/0098076 A1 | 5/2006 | Liang |
| 2007/0144634 A1 | 6/2007 | Hitchcock |
| 2008/0053476 A1 | 3/2008 | LaHood et al. |
| 2008/0152681 A1 | 6/2008 | Brown et al. |
| 2008/0176160 A1 | 7/2008 | Deprez et al. |
| 2009/0325221 A1 | 12/2009 | Long et al. |
| 2010/0031834 A1 | 2/2010 | Morgavi et al. |
| 2010/0086693 A1 | 4/2010 | Yamada et al. |
| 2011/0020023 A1 | 1/2011 | Hirai |
| 2011/0025040 A1 | 2/2011 | Dominguez |
| 2011/0141188 A1 | 6/2011 | Morita |
| 2011/0159463 A1 | 6/2011 | Samain |
| 2011/0164263 A1 | 7/2011 | Samain et al. |
| 2011/0268873 A1 | 11/2011 | Blette |
| 2012/0027423 A1 | 2/2012 | Kawai |
| 2012/0027443 A1 | 2/2012 | Kawai |
| 2012/0244316 A1 | 9/2012 | Dobler et al. |
| 2012/0244465 A1 | 9/2012 | Kobayashi |
| 2012/0307304 A1 | 12/2012 | Moreno |
| 2013/0216295 A1 | 8/2013 | Wong |
| 2014/0233967 A1 | 8/2014 | Suzuki |
| 2015/0053759 A1 | 2/2015 | Cahill et al. |
| 2015/0150767 A1 | 6/2015 | Klug et al. |
| 2015/0314141 A1 * | 11/2015 | Choi ..................... A45D 44/00 347/110 |
| 2016/0103962 A1 | 4/2016 | Costantino et al. |
| 2016/0316890 A1 | 11/2016 | Samain |
| 2016/0316891 A1 | 11/2016 | Samain |
| 2016/0316892 A1 | 11/2016 | Giron |
| 2016/0317403 A1 | 11/2016 | Giron |
| 2016/0324298 A1 | 11/2016 | Samain |
| 2016/0324299 A1 | 11/2016 | Samain |

FOREIGN PATENT DOCUMENTS

| | | |
|---|---|---|
| CN | 101010064 A | 8/2007 |
| CN | 101056605 A | 10/2007 |
| CN | 101686927 A | 3/2010 |
| CN | 101980694 A | 2/2011 |
| CN | 102490540 A | 6/2012 |
| EP | 705593 A1 | 4/1996 |
| EP | 0728460 A1 | 8/1996 |
| EP | 0749746 A1 | 12/1996 |
| EP | 0749747 A1 | 12/1996 |
| EP | 780114 A1 | 6/1997 |
| EP | 0923928 A1 | 6/1999 |
| EP | 0930060 A1 | 7/1999 |
| EP | 0938887 A1 | 9/1999 |
| EP | 1000607 A1 | 5/2000 |
| EP | 1048282 A1 | 11/2000 |
| EP | 1059047 A1 | 12/2000 |
| EP | 1304056 A2 | 4/2003 |
| EP | 1925278 A1 | 5/2008 |
| EP | 2090935 A1 | 8/2009 |
| FR | 2232303 A1 | 1/1975 |
| FR | 2759941 A1 | 8/1998 |
| FR | 2792192 A1 | 10/2000 |
| FR | 2858226 A1 | 2/2005 |
| FR | 2900594 A | 8/2007 |
| FR | 2905630 A1 | 3/2008 |
| FR | 2909844 A1 | 6/2008 |
| FR | 2939033 A1 | 6/2010 |
| JP | S62180000 A | 8/1987 |
| JP | S63-188616 A | 8/1988 |
| JP | H04-208997 A | 7/1992 |
| JP | H11-007203 A | 1/1999 |
| JP | H11169231 A | 6/1999 |
| JP | 2001-245945 A | 9/2001 |
| JP | 2001278739 A | 10/2001 |
| JP | 3266197 B2 | 1/2002 |
| JP | 2002-058528 A | 2/2002 |
| JP | 2002-148998 A | 5/2002 |
| JP | 2003006452 A | 1/2003 |
| JP | 2005040356 A | 2/2005 |
| JP | 2005-088434 A | 4/2005 |
| JP | 2007204487 A | 8/2007 |
| JP | 2008-127388 A | 6/2008 |
| JP | 2010-186133 A | 8/2010 |

(56) References Cited

FOREIGN PATENT DOCUMENTS

| | | |
|---|---|---|
| JP | 2012-002869 A | 1/2012 |
| JP | 2012072081 A | 4/2012 |
| JP | 2012-518457 A | 8/2012 |
| JP | 2012-520837 A | 9/2012 |
| JP | 2012249849 A | 12/2012 |
| JP | 2013-031504 A | 2/2013 |
| JP | 2013137758 A | 7/2013 |
| JP | 2013-252709 A | 12/2013 |
| WO | 1992007913 A1 | 5/1992 |
| WO | 9848659 A1 | 11/1998 |
| WO | 02/36083 A1 | 5/2002 |
| WO | 03033270 A1 | 4/2003 |
| WO | 2006/128737 A1 | 12/2006 |
| WO | 2006128737 A1 | 12/2006 |
| WO | 2007/134171 A1 | 11/2007 |
| WO | 2010/004526 A1 | 1/2010 |
| WO | 2010004526 A1 | 1/2010 |
| WO | 2010004531 A1 | 1/2010 |
| WO | 2010/095118 A | 8/2010 |
| WO | 2010/105842 A2 | 9/2010 |
| WO | 2012081065 A1 | 6/2012 |
| WO | 2013093889 A2 | 6/2013 |
| WO | 2013126513 A1 | 8/2013 |
| WO | 2013178701 A2 | 12/2013 |

OTHER PUBLICATIONS

Non-Final Office Action in U.S. Appl. No. 15/108,192 dated Oct. 6, 2017 (6 pages).
International Search Report for PCT/IB2014/067138 dated Mar. 11, 2015 (3 pages).
Dyno Pretty Pup: "Dyno Pretty Pup Beauty Diary: LA Colors 30 Eye Design Palettes—Review." Mar. 16, 2012 (4 pages).
Written Opinion Translation for PCT/IB2014/067138 (8 pages).
Office Action dated Jul. 2, 2018 issued in Japanese Patent Application No. 2016-543073 (17pp).
Office Action dated Jun. 5, 2018 issued in Chinese Patent Application No. 201480074439.7 (16 pp).
Restriction Requirement for U.S. Appl. No. 15/108,303 dated Sep. 6, 2017 (7 pages).
Office Action for JP App. No. 2016-543072 dated Dec. 17, 2018 with English Translation(7 pages).
Office Action for JP App. No. 2016-543056 dated Dec. 17, 2018 with English Translation (7 pages).
Office Action issued in Chinese Application No. 201480071272.9 dated Jul. 2, 2018 (14 pp).
Office Action issued in U.S. Appl. No. 15/108,295 dated Aug. 6, 2018 (56 pp).
Office Action issued in U.S. Appl. No. 15/108,151 dated Aug. 7, 2018 (60 pp).
Non-Final Office Action for U.S. Appl. No. 15/108,292 dated Jul. 7, 2017.
Office Action for JP App. No. 2016-543027, dated Dec. 21, 2018 with English Translation (13 pages).
Office Action for JP App. No. 2016-543057 dated Dec. 17, 2018 with English Translation (14 pages).
Office Action dated Sep. 10, 2018 in Japanese Patent Application No. 2016-542897 (7 pages).
Office Action dated Sep. 27, 2018 in U.S. Appl. No. 15/108,292 (16 pages).
Pubchem; castor oil—https://pubchem.ncbi.nlm.nih.gov/compound/castor_oil#section=Top; 1 page; 2010.
Office Action dated May 18, 2018 for Chinese Patent Application No. 2014800713416 (22 pages).
Non-Final Office Action for U.S. Appl. No. 15/108,302 dated Feb. 8, 2019 (7 pages).
Final Rejection for U.S. Appl. No. 15/108,295 dated Feb. 5, 2019 (10 pages).
Restriction Requirement for U.S. Appl. No. 15/108,305 dated Jan. 31, 2019 (8 pages).
English Translation of JP Office Action for JP Pat. App. No. 2016-542995 drafted Jan. 16, 2019 and dated Jan. 21, 2019 (3 pages).
First Office Action for CN Pat. Appln. No. 201480076509.2 with English Translation dated Oct. 30, 2017, 9 pages.
Final Rejection for U.S. Appl. No. 15/108,292 dated Jan. 30, 2018, 21 pages.
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes—Review, Dyno Pretty Pup, http://dynopupbeauty.blogspot.nl/2012/03/la-colors-30-eye-design-palettes-review.html, Mar. 16, 2012 (5 pages).
Notice of Allowance dated Nov. 13, 2018 issued in U.S. Appl. No. 15/108,303 (27 pages).
Restriction and Election of Species Requirement in U.S. Appl. No. 15/108,292 dated Mar. 1, 2017 (8 pages).
Non-Final Office Action in U.S. Appl. No. 15/108,076 dated Mar. 16, 2017 (12 pages).
"Papilio Laser Printable Temporary Tattoo Paper" (http://www.papilio.com/laser temporary tattoo paper.html,) Dec. 14, 2013 (3 pages).
"Cheap laser printer paper for toner transfer?" http://www.fountainpennetwork.com/forum/topic/41250-cheap-laser-printer-paper-for-toner-transfer/), Oct. 2, 2007 (11 pages).
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067133 dated Mar. 11, 2015 (5 pages).
International Search Report for PCT/IB2014/067134 dated Apr. 24, 2015 (4 pages).
International Search Report for PCT/IB2014/067136 dated Jul. 7, 2015 (5 pages).
Final Rejection for U.S. Appl. No. 15/108,151 dated May 20, 2019 (11 pages).
Non-Final Office Action for U.S. Appl. No. 15/108,305 dated May 15, 2019 (17 pages).
Final Rejection for U.S. Appl. No. 15/108,292 dated Apr. 26, 2019 (7 pages).
Non-Final Office Action for U.S. Appl. No. 15/108,295 dated Jun. 6, 2019 (12 pages).
Apr. 12, 2018 Office Action issued in U.S. Appl. No. 15/108,303.
Final Rejection for U.S. Appl. No. 15/108,302 dated Jul. 2, 2019 (7 pages).
Japanese Office Action for JP Pat. Appln. No. 2016-543057 dated Aug. 26, 2019 (8 pages).
Notice of Allowance for U.S. Appl. No. 15/108,292 dated Aug. 29, 2019 (16 pages).
Japanese Office Action for JP Pat. Appln. No. 2016-543056 dated Aug. 26, 2019 (8 pages).
Japanese Office Action for JP Pat. Appln. No. 2016-542996 dated Sep. 2, 2019 (14 pages).

* cited by examiner

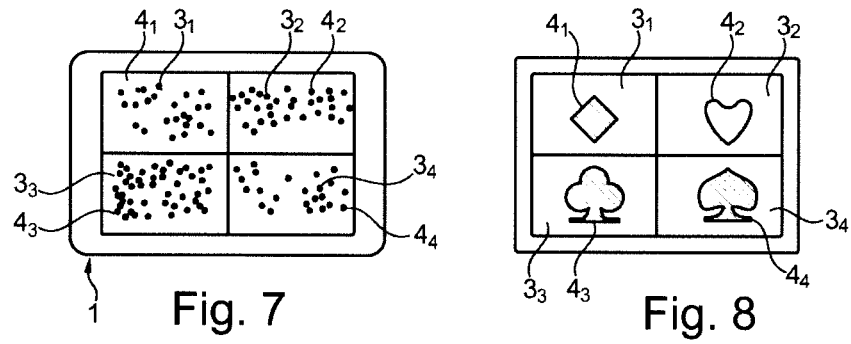
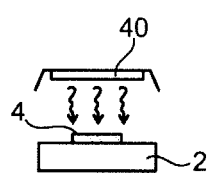
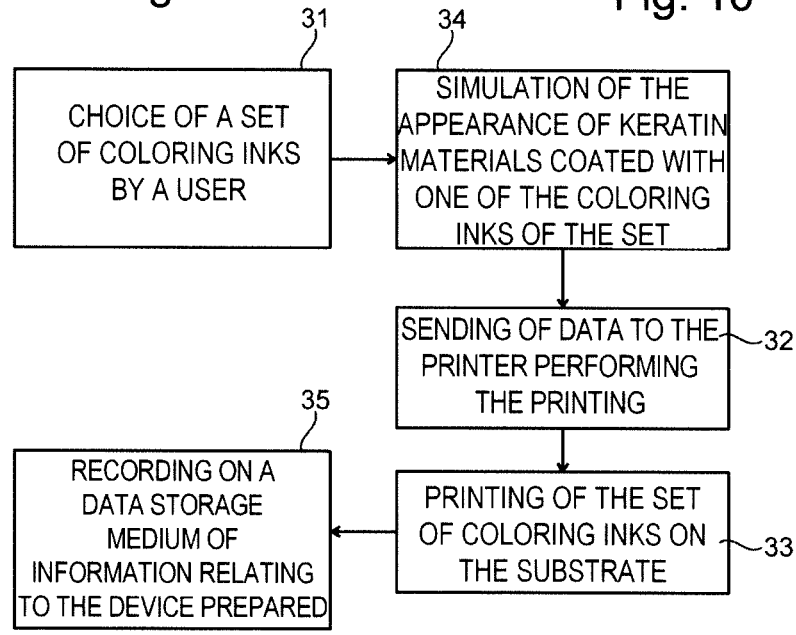

MAKEUP DEVICE COMPRISING A PLURALITY OF COSMETIC DYES

The present invention relates to a makeup device bearing one or more coloring inks deposited by printing.

BACKGROUND

The production of cosmetic patterns on the skin by using decal transfers requiring the addition of an intermediary liquid in order to obtain a transfer of the pattern onto the skin is known.

Other makeup devices such as palettes grouping together one or more different makeup compositions producing distinct colors are, moreover, known.

However, such devices provide users with a relatively limited range of colors not necessarily suitable for the user's taste. Such devices consequently limit the makeup effects that can be obtained and may not allow the user to customize their makeup at their pleasure. They may not be suitable for the various types of skin that exist.

There is a need to benefit from new makeup devices.

There is also a need to obtain makeup devices which make it possible to simply obtain complex and customized makeup results.

The invention is directed toward meeting all or some of these needs.

SUMMARY

According to a first aspect, the present invention relates to a makeup device comprising a substrate defining a printing surface having at least one region, in particular a plurality of regions, printed with at least one layer of at least one coloring ink intended to be applied to human keratin materials, said at least one layer of coloring ink
   having been deposited by printing on the printing surface by at least one printer,
   not being covered with an adhesive, and
   the coloring ink producing, after application and transfer to the keratin materials, at least one visible optical effect among color and/or brightness.

The device comprises for example a plurality of regions, each of the regions being printed with a layer of different cosmetic coloring ink, the coloring inks being intended to be applied to human keratin materials, the layers of ink having been deposited by printing on the substrate by at least one printer and not being covered with an adhesive, each coloring ink producing, after application to the keratin materials, at least one different visible optical effect chosen from color and brightness.

According to another of its aspects, the present invention relates to a makeup device comprising a substrate having at least one region, or a plurality of regions, each of the regions bearing a layer of different cosmetic coloring ink, the coloring inks being intended to be applied to human keratin materials and being capable of producing a makeup result by application to the keratin materials without addition of an intermediary fluid compound, each layer of coloring ink having been deposited by printing on the substrate by at least one printer and producing, after application to the keratin materials, at least one different visible optical effect chosen from color and brightness.

The invention makes it possible in particular to obtain makeup devices in the form of palettes prepared by printing cosmetic coloring inks.

The use of layers of coloring ink obtained by printing using a printer advantageously makes it possible, when compared with standard makeup devices, to obtain a complex and customizable makeup result.

A layer may comprise one or more inks. Two layers of ink may differ by the chemical nature of the ink(s) of which they are composed or by the relative proportions of each ink. The invention allows the user to choose their color(s), thus avoiding being restricted to limited, or even unsuitable, color choices. The richness of the colors offered to the user, permitted by the printing, makes it possible to obtain makeup results which produce a particularly attractive effect, and which resemble as closely as possible, for example, the natural or tanned complexion of the user.

The invention advantageously allows a user to create a customized makeup device bearing layers of coloring ink, at least one of which produces a color corresponding to the user's complexion, thus making possible to achieve a very natural makeup result.

All or some of the layers of coloring ink may comprise one or more colorants as described hereinafter.

Preferably, all or some of the layers of coloring ink present on the device are not entirely dry after a period of 15 minutes after the printing, in particular after a time of 24 hours and better still after a period of 7 days in contact with air and normal hygrometry (55% relative humidity) and 20° C., under atmospheric pressure.

The application, to the keratin materials, of a coloring ink from a not entirely dry layer facilitates the transfer of the ink.

All or some of the layers of coloring ink may be in fluid form when they are borne by the printing surface immediately before application to the keratin materials. It is possible for the coloring inks not to comprise pigment and/or particulate filler. This may facilitate the use of the technology of digital printing by inkjet.

Advantageously, the ink has a viscosity ranging from 1 mPa·s to 500 mPa·s and preferably from 1 mPa·s to 300 mPa·s at 25° C.

The viscosity of the ink may be measured via any process known to those skilled in the art, and in particular according to the following conventional process. At 25° C. using a Rheomat 180 viscometer, equipped with a spindle rotating at 200 rpm, those skilled in the art can select the spindle for measuring the viscosity from the spindles M1, M2, M3 and M4 on the basis of his general knowledge, so as to be able to perform the measurement.

In one variant, the ink is deposited in pulverulent form on the printing surface, for example by a laser printer having a deactivated fuser.

In one exemplary embodiment, a colorant is present in all or some of the coloring inks, in a weight content ranging from 0.01% to 60%, preferably ranging from 0.1% to 40% and preferentially ranging from 0.1% to 20% relative to the total weight of the ink. The colorant is preferentially constituted of one or more dyes.

In one exemplary embodiment, all or some of the coloring inks comprise a liquid solvent, for example water, in which the colorant is present, the liquid solvent being present in each of the coloring inks in a weight content ranging from 20% to 98%, or ranging from 30% to 90%, or else ranging from 40% to 80%.

In another exemplary embodiment, the coloring ink(s) does (do) not contain liquid solvent, in particular when a laser printer is used.

In one exemplary embodiment, the substrate of the device according to the invention comprises at least one translucent or transparent area. The translucent or transparent area can be totally or partly superposed with the layers of coloring ink. It may be useful for a transparent area of the substrate not to be coated with cosmetic ink, since this makes it possible to apply the substrate to the skin and to compare the color of the ink with that of the skin.

The layers of coloring inks may be superposed in their entirety on the translucent or transparent area. As a variant, only some of the layers of coloring inks are superposed on the transparent area.

The substrate may be made entirely of a transparent or translucent material. In this case, the translucent or transparent area extends over the entire surface of the substrate. As a variant, the substrate is opaque over all or part of its surface.

The substrate may be a flexible sheet or a rigid plate. It may be made of plastic (for example polyethylene or polystyrene). It may be woven or nonwoven. It may be made of organic or mineral material. It may be an aluminum foil.

In one exemplary embodiment, the substrate comprises one or more housings in which the layer(s) of coloring ink is (are) printed, which makes it possible to prevent mixing between two areas of different colors, in particular in the case of a very fluid ink or of an ink in powder form.

In one exemplary embodiment, several different cosmetic coloring inks are present within the same layer of ink. As a variant, all or some of the regions bear a layer formed from a single cosmetic coloring ink.

The coloring inks were advantageously deposited on the substrate by printing by at least one digital printer.

All or some of the layers of coloring ink obtained by printing may be printed in the form of raster spots and/or of raster lines, so as to form a halftone image, for example a monochromatic or polychromatic image.

The layer of coloring ink may comprise several coloring inks of different colors, each deposited in raster spots.

All or some of the coloring inks may be colored when observed under white light in the visible range (400 nm-800 nm). As a variant, the coloring inks are colorless under white light in the visible region, but may appear colored when subjected to a chemical and/or energy stimulus, such as exposure to UV (365 nm-400 nm), for example when the coloring ink contains a photochromic or fluorescent pigment.

When the printing surface comprises several regions, the coloring inks of each region differ from one another, preferably at least by the color that they produce after application to the keratin materials.

Use may be made of various types of coloring inks intended to be applied to various areas of the keratin materials.

All or some of the coloring inks may be skin makeup compositions, for example compositions intended to be applied to the cheeks or the eyelids. All or some of the coloring inks may thus be foundation or eyeliner or eyeshadow compositions.

All or some of the coloring inks may be lip makeup compositions, for example lipsticks or lip glosses.

All or some of the coloring inks may be eyelash makeup compositions, for example mascara compositions, or compositions for making up the hair, or compositions for masking body hair.

The coloring inks present on the same device may all be intended to be applied to the same area of the keratin materials, for example to the face. The coloring inks present on the same device are, for example, all foundation compositions. As a variant, the same device may comprise two layers of coloring ink which are each intended to be applied to a different area of the keratin materials. For example, a coloring ink of a first layer is intended to be applied to the skin and a coloring ink of a second layer, which is different than the ink of the first layer, is intended to be applied to the lips or the eyelashes.

Preferably, all or some of the coloring inks are capable of transferring onto the keratin materials without addition of an intermediary fluid compound, in particular of an intermediary liquid. In other words, all or some of the coloring inks may transfer onto the keratin materials by simple contact of the area intended to be made up with the coloring inks, without it being necessary to apply an intermediary liquid intended to improve the transfer of the inks, as in the case of decal transfers.

In one exemplary embodiment, at least one of the layers of coloring ink is printed on the printing surface of the substrate so as to form a pattern reproducing the appearance of relief and/or color heterogeneities of the skin.

The device may comprise a single region.

In one exemplary embodiment, the device comprises at least two, or even three, preferably at least four, regions on each of which a layer of coloring ink has been deposited by printing.

The device may or may not have one or more reliefs, for example such as ribs, separating all or some of the regions bearing the coloring inks. As a variant, the device does not comprise a relief separating the regions bearing the coloring inks.

In one exemplary embodiment, at least two regions bearing the layers of coloring ink are in contact. In particular, each of the regions bearing a layer of coloring ink is in contact with one or more other regions. As a variant, the regions bearing the layers of coloring ink are not in contact with one another.

The makeup device is preferably in the form of a palette. The makeup device may have a length/thickness ratio greater than or equal to 10.

The length corresponds to the largest dimension of the device measured when said device is observed from the front on the side of the surface bearing the coloring inks. The thickness corresponds to the largest dimension of the device when said device is observed from the side.

In one exemplary embodiment, the layers of coloring inks of several regions produce a gradation of the optical effect along a path connecting these regions and/or each of the regions is associated with an indicator, preferably borne by the substrate, making it possible to provide information on the location of the area of the keratin materials to which the coloring ink(s) borne by this region is (are) intended to be applied.

At least one colorimetric characteristic chosen from L, C*, h, a and b can continuously evolve between the various regions.

The various components of the color are defined in the colorimetric space CIE1976 (L*, a*, b*) or CIELAB. The value a* corresponds to the position on the red/green axis and the value b* corresponds to the position on the blue/yellow axis. The saturation C* corresponds to the amount $(a^{*a}+b^{*2})^{1/2}$. The hue angle h corresponds to the quantity arctan (a*/b*). L* denotes the lightness.

Advantageously, the layers of coloring ink produce a color gradation along a path connecting the regions.

The use of a device having a color gradation is advantageous since it allows a user to choose the color most suitable for the hue of the keratin materials intended to be made up.

The term "gradation of the optical effect along a path" should be understood to mean that the coloring inks have, along this path, at least two areas having a distinct degree of the optical effect, the variation in the degree of the optical effect being continuous or piecewise continuous between these two regions when one moves along said path.

The path may be linear. In other words, the coloring inks may have a gradation of the optical effect along one direction. As a variant, the path may be other than linear, for example in the form of a broken or curvilinear line, or even a sinusoidal line.

The presence of indicators providing information on the area of the keratin materials to be made up advantageously constitutes a tool which makes it possible to assist the user in producing the makeup result.

Colorant

The coloring ink may comprise one or more colorants chosen from water-soluble dyes, liposoluble dyes, pulverulent colorants such as pigments, in particular nacres, and glitter flakes, or alternatively coloring polymers.

The colorant(s) may be present in the coloring ink in a content ranging from 0.01% to 40% by weight, preferably from 0.1% to 30% by weight and preferentially ranging from 0.5% to 20% by weight relative to the total weight of the coloring ink.

The term "pigments" should be understood to mean white or colored, mineral or organic particles of any form, which are insoluble in the cosmetic medium, and which are intended to color the coloring ink.

The term "nacres" should be understood to mean iridescent particles of any form, in particular produced by certain molluscs in their shell, or else synthesized.

The pigments may be white or colored, and mineral and/or organic. Among the mineral pigments that may be mentioned are titanium dioxide, optionally surface-treated, zirconium oxide or cerium oxide, and also zinc oxides, iron (black, yellow or red) oxides or chromium oxides, manganese violet, ultramarine blue, chromium hydrate and ferric blue, and metal powders, for instance aluminum powder and copper powder.

Among the organic pigments that may be mentioned are carbon black, pigments of D&C and FD&C type and lakes based on cochineal carmine or on barium, strontium, calcium or aluminum.

The nacreous pigments may be chosen from white nacreous pigments such as mica coated with titanium or with bismuth oxychloride, colored nacreous pigments such as titanium mica coated with iron oxides, titanium mica coated in particular with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue. Among the liposoluble dyes, mention may be made of Sudan Red III (CTFA: D&C Red 17), lutein, quinizarine green (CTFA: D&C Green 6), alizurol purple SS (CTFA: D&C Violet 2), Sudan brown, D&C Yellow 11, D&C Orange 5, quinoline yellow, curcumin, carotenoid derivatives such as lycopene, beta-carotene, bixin or capsanthin, and mixtures thereof. The dyeing polymers are generally copolymers based on at least two different monomers, at least one of which is a monomeric organic dye. Such polymeric dyes are known to those skilled in the art. Reference may be made, for example, to the following documents: U.S. Pat. Nos. 5,032,670; 4,999,418; 5,106,942; 5,030,708; 5,102,980; 5,043,376; 5,104,913; 5,281,659; 5,194,463; 4,804,719; WO 92/07913 or EP 1 048 282.

The coloring ink may comprise one or more colorants, in particular photochromic pigments, i.e. colorants which have the property of changing color when they are irradiated with a light source of a certain frequency, and then of regaining their initial color, or a similar color, when the irradiation is stopped. Among the photochromic colorants, mention may be made in particular of:

complex mineral photochromic compounds and more particularly doped aluminosilicates and metal oxides and metal oxide hydrates, such as those described in WO-A-02/36083;

photochromic naphthopyran compounds, in particular 3H-naphtho[2,1-b]pyrans or 2H-naphtho[1,2-b]pyrans, for instance 3,3-bis(4-methoxyphenyl)-6-morpholino-3H-naphtho[2,1-b]pyran, 3-phenyl-3-(4-morpholinophenyl)-6-morpholino-3H-naphtho[2,1-b]pyran, 3-phenyl-3-(4-piperidinophenyl)-6-morpholino-3H-naphtho[2,1-b]pyran, 3-phenyl-3-(4-piperidinophenyl)-6-carboxymethyl-9-N-dimethyl-3H-naphtho[2,1-b]pyran or 2-phenyl-2-(4-piperidinophenyl)-5-carboxymethyl-9-N-dimethyl-2H-naphtho[1,2-b]pyran. Such compounds are described in patent application EP-A-1 410 785;

diarylethene or fulgide compounds such as those described in patent application EP-A-938 887.

The coloring ink may also comprise one or more fillers, in particular in a content ranging from 0.01% to 50% by weight, relative to the total weight of the coloring ink, preferably ranging from 0.01% to 30% by weight.

The term "fillers" should be understood as meaning colorless or white, mineral or synthetic particles of any shape, which are insoluble in the medium of the coloring ink, irrespective of the temperature at which this ink is manufactured.

These fillers serve in particular to modify the rheology or texture of the coloring ink.

The fillers may be mineral or organic and of any shape, platelet-shaped, spherical or oblong, irrespective of the crystallographic form (for example lamellar, cubic, hexagonal, orthorhombic, etc.). Mention may be made of talc, mica, silica, kaolin, polyamide (Nylon®) powder (Orgasol® from Atochem), poly-β-alanine powder and polyethylene powder, tetrafluoroethylene polymer (Teflon®) powder, lauroyllysine, starch, boron nitride, hollow polymer microspheres such as polyvinylidene chloride/acrylonitrile microspheres, for instance Expancel® (Nobel Industrie), acrylic acid copolymer microspheres (Polytrap® from the company Dow Corning) and silicone resin microbeads (for example Tospearls® from Toshiba), elastomeric polyorganosiloxane particles, precipitated calcium carbonate, magnesium carbonate, magnesium hydrogen carbonate, hydroxyapatite, hollow silica microspheres (Silica Beads® from Maprecos), glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

The coloring ink may also comprise an additional polymer such as a film-forming polymer. The term "film-forming polymer" is intended to mean a polymer that is capable of forming, by itself or in the presence of an auxiliary film-forming agent, a continuous film that adheres to a support, in particular to keratin materials. Among the film-forming polymers that may be used in the coloring ink, mention may be made of synthetic polymers, of radical type or of polycondensate type, polymers of natural origin and mixtures thereof, in particular acrylic polymers, polyurethanes, polyesters, polyamides, polyureas, and cellulose-based polymers, for instance nitrocellulose.

Needless to say, those skilled in the art will take care to select this or these optional additional compound(s), and/or the amount thereof, such that the advantageous properties of the coloring ink are not, or are not substantially, adversely affected by the envisaged addition.

Cosmetically Acceptable Medium

The coloring ink according to the invention constitutes a cosmetically acceptable medium, i.e. a medium that is compatible with keratin materials such as the skin of the face or the body, the lips, the hair, the eyelashes, the eyebrows and the nails.

In one exemplary embodiment, all or some of the coloring inks also comprise a transfer compound having a boiling point of greater than or equal to 120° C., in particular ranging from 120° C. to 350° C. and in particular ranging from 120° C. to 300° C.

In another exemplary embodiment, all or some of the coloring inks also comprise a transfer compound having a boiling point of greater than or equal to 200° C., in particular ranging from 200° C. to 350° C.

The ink may also contain water.

The transfer compound is advantageously in liquid form at ambient temperature (25° C.).

The transfer compound(s) are preferably chosen from: glycerol (boiling point: 290° C.), ethylene glycol (boiling point: 197° C.), diethylene glycol (boiling point: 245° C.), triethylene glycol (boiling point: 285° C.), 1,5-pentanediol (boiling point: 242° C.), 1-pentanol (boiling point: 138° C.), 1-hexanol (boiling point: 157° C.), benzyl alcohol (boiling point: 205° C.), 1-hexanal (boiling point: 130° C.), 1-heptanal (boiling point: 153° C.), 2-pyrrolidone (boiling point: 245° C.), N-methyl-2-pyrrolidone (boiling point: 203° C.), N-ethylpyrrolidine (boiling point: 211° C.), propylene carbonate (boiling point: 240° C.), 1,3-diaminopropane (boiling point: 140° C.), 2-imidazolidinone (boiling point: 131° C.), 2-amino-1-butanol (b.p.=178° C.), 2-aminopropanol (boiling point: 173° C.), ethanolamine (boiling point: 171° C.), butyl acetate (boiling point: 126° C.), and mixtures thereof.

According to a first embodiment of the invention, the transfer compound(s) are miscible in water at 25° C. (in particular having a solubility in water of at least 5% by weight), and are preferably chosen from $C_5$-$C_6$ monoalcohols, $C_2$-$C_6$ polyols, $C_6$-$C_{10}$ esters, $C_5$-$C_8$ ketones (in particular cyclic ketones), $C_6$-$C_7$ aldehydes, $C_3$-$C_8$ cyclic carbonates, $C_3$-$C_8$ cyclic ureas, $C_2$-$C_6$ amino alcohols, $C_3$-$C_6$ diamines, water-miscible amino silicones such as Silicone Quaternium-8 (INCI name) sold, for example, under the name Silsense Q-Plus Silicone by Noveon, PEG-7 Amodimethicone (INCI name) sold, for example, under the name Silsense A-21 Silicone by Noveon, and mixtures thereof.

The coloring ink may comprise a plurality of different transfer compounds, preferably at least three different transfer compounds, preferably at least four different transfer compounds, the transfer compounds each having a boiling point of greater than or equal to 120° C., in particular ranging from 120° C. to 350° C.

In one exemplary embodiment, the transfer compounds comprise a mixture of at least two different $C_2$-$C_6$ polyols, in particular of at least three different $C_2$-$C_6$ polyols and in particular of at least four different $C_2$-$C_6$ polyols.

According to a second embodiment of the invention, the transfer compound(s) are immiscible in water (solubility in water at 25° C. of less than 5% by weight). Such transfer compounds may be chosen from the volatile or non-volatile oils usually used in cosmetics, which may be chosen from natural or synthetic carbon-based, hydrocarbon-based or fluoro oils, which are optionally branched, alone or as a mixture.

The term "non-volatile oil" is intended to mean an oil that is capable of remaining on the skin at ambient temperature and atmospheric pressure for at least one hour, and in particular having a non-zero vapor pressure at ambient temperature (25° C.) and atmospheric pressure of less than 0.01 mmHg (1.33 Pa).

Mention may be made in particular of non-volatile carbon-based oils, in particular hydrocarbon-based oils of plant, mineral, animal or synthetic origin, such as liquid paraffin (or petroleum jelly), squalane, hydrogenated polyisobutene (Parleam oil), perhydrosqualene, macadamia oil, soybean oil, sweet almond oil, beauty-leaf oil, palm oil, grapeseed oil, sesame oil, corn oil, arara oil, rapeseed oil, sunflower oil, cotton oil, apricot oil, castor oil, avocado oil, jojoba oil, olive oil, cereal germ oil or shea butter oil; linear, branched or cyclic esters containing more than 6 carbon atoms, in particular 6 to 30 carbon atoms, such as esters of lanolic acid, of oleic acid, of lauric acid or of stearic acid; esters derived from long-chain acids or alcohols (i.e. containing from 6 to 20 carbon atoms), in particular the esters of formula RCOOR' in which R represents a higher fatty acid residue comprising from 7 to 19 carbon atoms and R' represents a hydrocarbon-based chain comprising from 3 to 20 carbon atoms, in particular $C_{12}$-$C_{36}$ esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, bis(2-ethylhexyl) succinate, diisostearyl malate, and glyceryl or diglyceryl triisostearate; higher fatty acids, in particular of $C_{14}$-$C_{22}$, such as myristic acid, palmitic acid, stearic acid, behenic acid, oleic acid, linoleic acid, linolenic acid or isostearic acid; higher fatty alcohols, in particular of $C_{16}$-$C_{22}$, such as cetanol, oleyl alcohol, linoleyl alcohol or linolenyl alcohol, isostearyl alcohol or octyldodecanol; and mixtures thereof.

Mention may also be made of decanol, dodecanol, octadecanol, liquid fatty acid triglycerides of 4 to 10 carbon atoms such as heptanoic or octanoic acid triglycerides, caprylic/capric acid triglycerides; linear or branched hydrocarbons, of mineral or synthetic origin such as liquid paraffins and derivatives thereof, petroleum jelly, polydecenes and hydrogenated polyisobutene such as Parleam; synthetic esters and ethers in particular of fatty acids, for instance purcellin oil, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate or fatty alkyl heptanoates, octanoates and decanoates; polyol esters such as propylene glycol dioctanoate, neopentyl glycol diheptanoate or diethylene glycol diisononanoate; and pentaerythritol esters; fatty alcohols containing from 12 to 26 carbon atoms, such as octyldodecanol, 2-butyloctanol, 2-hexyldecanol or 2-undecylpentadecanol.

Among the volatile compounds, mention may be made of non-silicone volatile oils, in particular $C_8$-$C_{16}$ isoparaffins, such as isododecane, isodecane and isohexadecane.

More preferentially, mention may be made of volatile or non-volatile alkanes that are liquid at ambient temperature, and more particularly decane, heptane, dodecane, isododecane, isohexadecane, cyclohexane and isodecane, and mixtures thereof.

Among the water-immiscible transfer compound(s), use may be made of isododecane (boiling point: 180° C.), isopropyl myristate (boiling point: 168° C.), isostearyl alcohol (boiling point: 331° C.), isodecyl neopentanoate (boiling point: 272° C.), isononyl isononanoate (boiling point: 285° C.), oleyl alcohol (boiling point: 315° C.), 2-octyldodecanol (boiling point: 358° C.), isopropyl palmitate (boiling point: 340° C.), isopropyl isostearate (boiling point: 361° C.), and mixtures thereof.

The coloring ink according to the invention may also comprise waxes.

The term "wax" is intended to mean a lipophilic compound, which is solid at ambient temperature (25° C.), with a reversible solid/liquid change of state, with a melting point of greater than or equal to 30° C., which may be up to 120° C. By bringing the wax to the liquid state (melting), it is possible to make it miscible with the oils that may be present and to form a microscopically homogeneous mixture, but on returning the temperature of the mixture to ambient temperature, recrystallization of the wax in the oils of the mixture is obtained. The melting point of the wax may be measured using a differential scanning calorimeter (DSC), for example the calorimeter sold under the name DSC 30 by the company Mettler.

The waxes may be hydrocarbon-based waxes, fluoro waxes and/or silicone waxes, and may be of plant, mineral, animal and/or synthetic origin. In particular, the waxes have a melting point of greater than 25° C. and better still greater than 45° C. As wax that may be used in the coloring ink, mention may be made of beeswax, carnauba wax or candelilla wax, paraffin, microcrystalline waxes, ceresin or ozokerite; synthetic waxes such as polyethylene waxes or Fischer-Tropsch waxes, silicone waxes such as alkyl or alkoxy dimethicones containing from 16 to 45 carbon atoms.

The nature and amount of the waxes depend on the desired mechanical properties and textures. As a guide, the coloring ink may contain from 0.01% to 30% by weight and better still from 1% to 20% by weight of waxes relative to the total weight of the coloring ink.

The coloring ink advantageously comprises a mixture of a plurality of transfer compounds, each being miscible in water at 25° C. As a variant, the coloring ink comprises a mixture of a plurality of transfer compounds, each being water-immiscible. As another variant, the coloring ink comprises a mixture of a plurality of transfer compounds and comprises both one or more water-miscible transfer compounds and one or more water-immiscible transfer compounds.

In one exemplary embodiment, the coloring ink also comprises an organic solvent that is liquid (at 25° C.) with a boiling point of less than 120° C. As examples of such organic solvents, mention may be made of n-hexane (boiling point: 69° C.), cyclohexane (boiling point: 81° C.), ethyl acetate (boiling point: 76° C.), n-heptane (boiling point: 98° C.), isobutyl acetate (boiling point: 116° C.), methyl acetate (boiling point: 57° C.), ethanol (boiling point: 78° C.), butanol (boiling point: 117° C.), isopropanol (boiling point: 81° C.), n-propanol (boiling point: 97° C.), and mixtures thereof.

Unless otherwise mentioned, all the boiling points are measured at atmospheric pressure, i.e. 1013.25 mbar (corresponding to a pressure of 1013.25 hectopascal (hPa)).

The coloring ink may be in the form of an aqueous solution, an aqueous gel or an emulsion.

In one exemplary embodiment, the coloring ink comprises a wax, and the ink is softened, for example, at the time of use by placing it in the vicinity of a heating member.

The wax is for example brought to a temperature of between 30° C. and 60° C. before being applied to the keratin materials. As a variant, the wax is brought to a temperature of between 30° C. and 60° C. while it is in contact with the area of the keratin materials intended to be made up.

When a coloring ink is intended to be brought to a temperature of between 30° C. and 60° C. prior to its application, the coloring ink brought to this temperature may be applied to the nails so as to produce a makeup result thereon.

The coloring ink may be brought to a temperature of between 30° C. and 60° C. by being placed close to a heating member. As a variant, the coloring ink obtained just after printing may already be at such a temperature; the user can then apply to the keratin materials the coloring ink at this temperature, before it cools.

In one exemplary embodiment, the substrate is made of a nonabsorbant material, for example made of plastic. The substrate is advantageously non-porous, at least on the face intended to receive the coloring inks.

The substrate may or may not be flat.

In one exemplary embodiment, one or more of the regions bearing one or more coloring inks are detachable from a part of the substrate.

In one exemplary embodiment, the substrate comprises information regarding the nature of the keratin materials intended to be made up with all or some of the coloring inks. This information may be printed with the same ink or otherwise as one of those present on the substrate.

In one exemplary embodiment, when one or more of the coloring inks are intended to be applied by transfer to the cheeks and/or the nails, the substrate may have a thickness of greater than or equal to 1 mm, in particular greater than or equal to 3 mm, in particular ranging from 1 to 5 mm.

In one exemplary embodiment, when one or more of the coloring inks are intended to be applied by transfer to the periocular region and/or to the lips, the substrate may have a thickness of greater than or equal to 3 mm, in particular greater than or equal to 1 mm, in particular ranging from 3 to 20 mm.

In one exemplary embodiment, when one or more of the coloring inks are intended to be applied by transfer to the nose and/or in the region of the ears, the substrate may have a thickness of greater than or equal to 1 cm, in particular greater than or equal to 3 cm, in particular ranging from 1 to 4 cm.

The thickness of the abovementioned substrate corresponds to its maximum dimension measured perpendicular to the surface bearing the coloring inks intended to be applied by transfer to the keratin materials.

Thus, the substrate advantageously has a thickness adapted to the area of keratin materials to be made up.

According to another of its aspects, the present invention relates to a process for preparing a device as defined above, comprising the step consisting in depositing a cosmetic coloring ink or a plurality of different cosmetic coloring inks on a region or a plurality of regions of a substrate, using at least one printer.

The printer may be an inkjet printer, for example a thermal or piezoelectric printer, a sublimation printer or a 3D printer or a laser printer, in particular having a deactivated fuser. The printer may be a food-grade inkjet printer of the Gatocopy A426 machine type allowing printing onto non-flat objects.

In one example, the printer is a laser printer arranged to allow the formation by electrophotography or magnetophotography of a layer of ink having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood as meaning a pulverulent cosmetic composition that is compatible with the formation of an image via an electrophotographic or magnetophotographic process as used in laser printers. Preferably, it is a toner that is suitable for electrophotographic use.

The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

When the ink is in the form of a cosmetic toner, this toner may comprise, besides a coloring agent, a compound for controlling the electrical charge, a particular additional filler, a lubricant, a wax and/or a binder.

Preferably, the particles of the toner have a mean size of between 1 and 16 μm. The toner comprises, for example, pigments with a particle size of between 1 and 10 μm.

Advantageously, the printing uses several inks of different colors.

The printing may use at least three, in particular at least four, five, six, seven, eight, nine, ten, eleven or twelve coloring inks of different colors.

The printing may use only coloring inks produce primary colors. As a variant, the printing uses both coloring inks corresponding to primary colors and at least one coloring ink corresponding to a non-primary color.

The printing of the coloring inks may be three-color or four-color printing.

In one exemplary embodiment, the process comprises a step of choosing a set of coloring inks to be printed by a user and of transmitting, by means of a machine connected to at least one printer that performs the printing, information relating to this set.

The machine may be a computer, an advanced portable telephone, also known as a "smartphone", or a tablet computer. The machine may be connected physically and/or by means of a data exchange network to said printer.

In one exemplary embodiment, the process comprises a step of recovering information relating to the nature of the layer of coloring ink to be printed, stored on a computer medium, the printing being carried out according to this information.

For example, the process comprises a step of choosing, by a user, a set of coloring inks to be printed among several sets of coloring inks proposed to the user, information relating to the sets proposed being stored on a computer medium, the process also comprising a step of transmitting, by means of a machine connected to at least one printer that performs the printing, information relating to the set chosen.

The machine may be connected physically and/or by means of a data exchange network to the computer medium.

The invention advantageously offers the possibility of exchanging between users files relating to the makeup devices to be printed.

Thus, the user can choose a coloring ink or a set of coloring inks to be printed from several sets of coloring inks proposed, these sets having been created by artists and/or by other users.

In one exemplary embodiment, one or more sets of coloring inks to be printed and also makeup advice associated with these sets can be proposed to the user. The makeup advice can provide information on the way to apply the coloring inks to the keratin materials and/or on the area of keratin materials to be made up and/or can propose an additional makeup composition intended to be applied in combination with all or some of the coloring inks to be printed.

In one exemplary embodiment, the user receives customized advice on the makeup device to be produced. For example, the user receives a computer file providing information on the optical effect produced by the coloring inks of the layers to be printed and/or on the nature of said inks and/or on the area of the keratin materials to which the coloring inks of the layers are intended to be applied. The computer file can be transmitted to the user by means of a data exchange network, for example via the Internet.

As a variant, the user designs the makeup device to be prepared and transmits for production of the device a computer file providing information on the optical effect produced after application to the keratin materials by the coloring inks of the layers to be printed and/or the nature of said inks and/or the area of the keratin materials to which the coloring inks are intended to be applied. The device can then be prepared automatically from the file transmitted.

In one exemplary embodiment, the process comprises, before printing, a step of simulating the appearance of the keratin materials coated with one or more of the coloring inks to be printed, the simulation of the appearance of the keratin materials coated being displayed on a screen of a machine.

Advantageously, such a simulation allows users to see themselves on the screen in makeup configurations, thus helping them to optimize their makeup device to be printed.

In one exemplary embodiment, the choice of the coloring inks is made according to information relating to the appearance of the keratin materials to be made up, in particular after performing an acquisition of at least one image of the keratin materials to be made up and/or performing at least one measurement of at least one optical characteristic of these keratin materials.

In one exemplary embodiment, the process comprises a step of recording, on a data storage medium, information relating to the device prepared, the information preferably relating to the nature of the coloring inks present on the device prepared and/or to the nature of the keratin materials intended to be coated with all or some of the coloring inks of the device prepared.

Thus, the invention advantageously allows the user to remember their ideal makeup device. The use of a printer then gives the user a perfect reproducibility at each new printing.

In one exemplary embodiment, said at least one printer performs a first round of printing making it possible to obtain a first fraction of the deposit of the coloring inks and then at least one second round of printing making it possible to obtain a second fraction of the deposit of the coloring inks superposed on the first fraction. Thus, in order to print the layer(s), the coloring inks can be deposited in several rounds of printing.

Performing several rounds of printing can make it possible, by increasing the amount of coloring inks deposited on the substrate, to improve the duration of use of the devices according to the invention.

In one exemplary embodiment, all or some of the coloring inks printed form a pattern that is transferable onto the keratin materials. The pattern may be transferred by pressing the printing surface of the substrate onto the keratin materials, with a finger or with an applicator such as a roll, a brush, a fine brush, or a sponge, in particular made of synthetic foam.

The pattern formed by the coloring inks may comprise several areas of different colors. As a variant, the pattern is a flat color tint.

As a variant, the coloring inks may form a color gradation and are particularly intended to be applied in the periocular area. As a variant, all or some of the coloring inks form a pattern reproducing the appearance of relief and/or color heterogeneities of the skin, for example a skin grain or freckles, or else false eyebrows. In this case, the application can be carried out by transfer, in order to preserve the printed pattern.

The substrate may be reusable. For example, printing is performed on the substrate, which is accessible, but does not leave the printer. Thus, after use, the printer can reintegrate the substrate, clean it and make it ready for a new print.

According to another of its aspects, the present invention relates to a process for making up human keratin materials, comprising the step consisting in applying all or some of at least one coloring ink present on a device according to the invention to the human keratin materials, in particular to the skin, in particular to the cheek and/or the eyelids.

In one exemplary embodiment, the keratin materials intended to be coated with all or some of the coloring inks have not been covered, before application, with an intermediary fluid compound intended to improve the application of the coloring inks and/or the process lacks a step of addition, to all or some of the coloring inks borne by the substrate, of an intermediary fluid compound intended to improve the application.

Thus, the area of the keratin materials that is intended to be made up has advantageously not been pretreated at the time of application.

As a variant, the area of the keratin materials that is intended to be made up has been covered, before application, with an intermediary fluid compound, for instance ethanol or isododecane, making it possible to improve the application of all or some of the coloring inks, and/or an intermediary fluid compound intended to improve the application has been added to all or some of the coloring inks borne by the substrate before application.

In one exemplary embodiment, the addition of the intermediary fluid compound making it possible to improve the application makes it possible only to dissolve or to make more fluid all or some of the coloring inks and not, for example, the substrate of the makeup device and/or a layer of adhesive optionally present.

In one exemplary embodiment, a plurality of coloring inks are mixed before application to the keratin materials and all or some of the mixture is applied to the keratin materials.

The coloring inks can be mixed on the substrate, for example in an area of the substrate initially bearing no coloring ink or, as a variant, can be mixed on a support which is not interlinked with the substrate.

In one exemplary embodiment, all or some of the coloring inks are applied to a region of the keratin materials exhibiting a color heterogeneity, for example a mark or dyschromia for example present on the face.

In one exemplary embodiment, coloring ink taken from a first layer is applied to a first area of the keratin materials and coloring ink taken from a second layer, different than the first, is applied to a second area of the keratin materials, different than the first.

The makeup result obtained can result from the juxtaposition of several coloring inks on the keratin materials, for example on the face.

As a variant, it is possible, firstly, to deposit several coloring inks in a juxtaposed manner on the keratin materials, and then to mix the latter in order to obtain the makeup result.

As a variant, it is possible, firstly, to deposit several coloring inks in a juxtaposed manner on the keratin materials, for example on the eyelid and/or the cheeks, and then to spread all or part of the deposits of coloring inks produced, for example in order to obtain a gradation effect. Advantageously, the coloring inks deposited do not mix after the spreading.

In one exemplary embodiment according to the invention, the process also comprises a step of finishing the makeup obtained on the keratin materials, for example so as to attenuate the demarcations between a made-up area and an area not made up. The finishing of the makeup obtained may comprise a step of spreading one or more coloring inks in order to produce shading-off, for example.

The finishing can be carried out by exerting a friction on just one part of the makeup produced, for example its upper part in the case of makeup produced on the eyelid.

When all or some of the coloring inks form a pattern intended to transfer onto the keratin materials, the user can carry out finishing before the transfer of the coloring inks onto the keratin materials.

In one exemplary embodiment, the process thus comprises a step of finishing the pattern formed by the coloring inks borne by the substrate, the finishing being carried out for example by exerting a friction on just one part of the pattern, for example its upper part in the case of a pattern intended to be applied to the eyelid.

In one exemplary embodiment, the process also comprises a step of applying an additional cosmetic composition, different than the coloring inks, said additional cosmetic composition preferably being proposed to the user by a machine according to the nature of at least one of the coloring inks present on the device and/or to the nature of the keratin materials intended to be coated with all or some of the coloring inks of the device.

The use of such an additional composition advantageously makes it possible to obtain particularly attractive makeup results, and for example to obtain attractive tanning and/or shadowing effects.

In one exemplary embodiment, the coloring ink is taken from the device using an applicator and is applied to the keratin materials using said applicator.

The applicator can be chosen from an applicator roll, an applicator pad, a sheet element, a patch, a mask, a porous foam, a sponge, a wipe, a brush, a fine brush, a spatula or a flocked tip.

The applicator may retain the coloring ink by capillary action.

As a variant, all or some of the coloring inks present on the substrate are applied by transfer onto the keratin materials.

In one exemplary embodiment, the application of the coloring ink to the keratin materials is carried out without bringing the coloring ink into contact with an intermediary fluid compound, in particular an intermediary liquid.

According to another of its aspects, the present invention relates to a cosmetic assembly comprising, within the same packaging, a makeup device as defined above and an applicator for the application of all or some of the coloring inks to human keratin materials.

According to yet another of its aspects, the present invention relates to a cosmetic assembly comprising, in the same packaging, a plurality of different makeup devices according to the invention, as defined above.

The makeup devices can differ by virtue of the nature of the inks that they bear, in particular by virtue of the colors thereof.

According to yet another of its aspects, the present invention relates to a cosmetic assembly comprising, in the same packaging, a makeup device as defined above and an additional cosmetic composition, in particular makeup composition, intended to be applied in combination with all or some of the coloring inks borne by the device.

DESCRIPTION OF THE FIGURES

The invention may be better understood on reading the following description of non-limiting implementation examples thereof, and with reference to the attached drawing, in which:

FIGS. 4 to 8 represent variants of makeup devices according to the invention, FIGS. 9 and 10 show variants of makeup processes according to the invention, FIG. 11 is a block diagram illustrating steps of a variant of a process for preparing a device according to the invention.

FIG. 1 represents an example of a makeup device 1 according to the invention. The device 1 comprises a substrate 2 having a printing surface 3 divided up into several regions $3_1, \ldots, 3_4$ each comprising a layer of different cosmetic coloring ink $4_1, \ldots, 4_4$. As shown, the layers of coloring inks $4_1, \ldots, 4_4$ can be of various colors, for example of the same shade and of different saturation, or of different shades and the same saturation, or of different shades and saturations.

The substrate 2 is preferably made of a flexible material. As a variant, the substrate 2 is made of a rigid or semi-rigid material.

All or part of the face of the substrate 2 placed on the side of the layers of coloring inks $4_1, \ldots, 4_4$ is preferably smooth and has a roughness of less than or equal to 1 mm, in particular of between 1 and 100 μm, preferably of less than or equal to 50 μm. The roughness is measured using a roughness meter, the tip of which has a radius of curvature of 10 mm, and the force of which, applied to the material to be characterized, is 6 mN.

As illustrated, regions $3_1, \ldots, 3_4$ are in contact with one another and are not separated by reliefs.

The resolution of the printing at the level of all or some of the layers of coloring inks $4_1, \ldots, 4_4$ may be between 16 dpi and 1600 dpi.

Figures 1, 2:
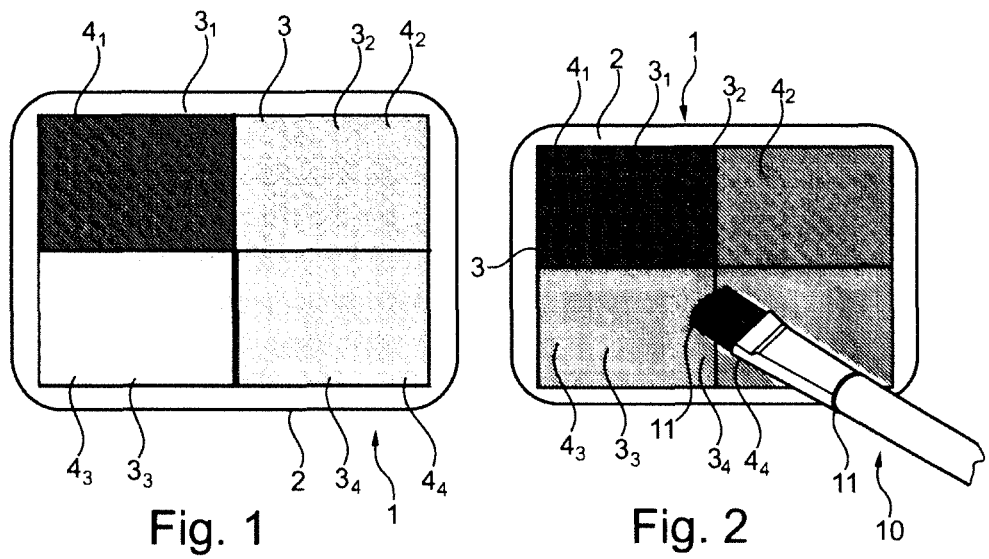
FIG. 1 represents an example of a makeup device according to the invention.
FIG. 2 shows the implementation of a makeup process according to the invention.

In the example of FIG. 1, each ink is deposited in the form of a flat color tint, spread over an area for example greater than or equal to 2 cm$^2$.

The color of a layer $4i$ may result from a subtractive synthesis of elementary colors deposited on the corresponding region, these elementary colors each being deposited by printing, in the form of raster spots for example. As a variant, a single ink is deposited on a region and the color of the layer corresponds to the actual color of the ink that is deposited.

For example, in order to create, on a region, a layer of red-colored ink, it is possible to apply to the substrate an intrinsically red ink, or magenta and yellow inks in the form of superimposed raster spots.

The sampling of coloring ink from a layer $4i$ printed in a region $3i$ of the device 1 of FIG. 1 can be carried out, as illustrated in FIG. 2, using an applicator 10 comprising a gripping part 12 and an applying part 11. The applicator 10 can, as illustrated, be in the form of a fine brush.

The applying part 11 thus loaded with coloring ink(s) is then brought into contact with the keratin materials to be made up. The user can, before application, mix, using the applying part 11, several layers of coloring ink $4_1, \ldots, 4_4$ present on different regions and apply the resulting mixture to the keratin materials. The mixing can be carried out on the printing surface 3 of the substrate 2 or on a distinct support, or even in situ on the skin.

Figure 3:
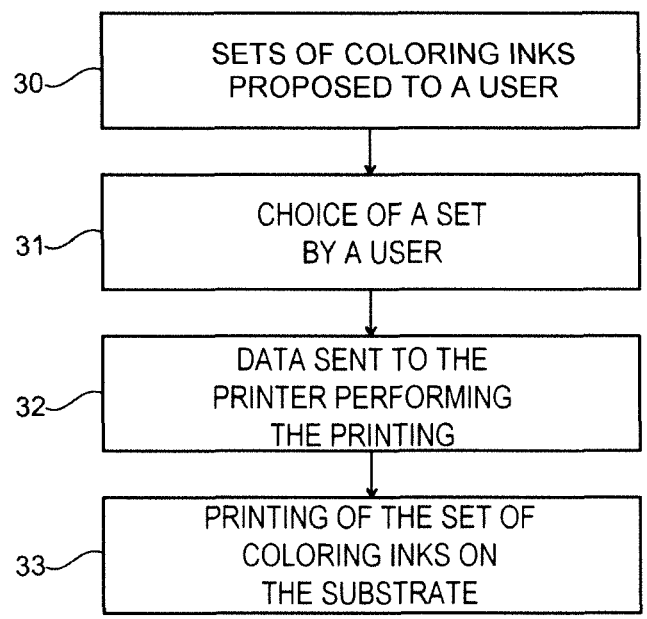
FIG. 3 is a block diagram illustrating steps of a process for preparing a makeup device according to the invention.

An example of a process for manufacturing a device according to the invention will now be described, with reference to FIG. 3.

In a first step 30, various sets of coloring inks are proposed to the user, for example by displaying on a screen of a machine. Step 31 of choice of the set of coloring inks to be printed by the user can be carried out on a touchscreen for example.

The machine may also be arranged to provide the user with a simulation of the makeup result. Thus, the machine may display a simulation of the appearance of the keratin materials made up with one or more of the coloring inks of the set chosen. To do this, the machine may acquire at least one image of the keratin materials to be made up.

In one variant, the user makes a computer file listing the set of coloring inks that he or she wishes to print.

Once the set of coloring inks has been chosen, the machine in step 32 sends to the printer the data required for printing the coloring inks on the substrate.

The machine may be connected physically and/or by means of a network to the printer performing the printing.

Once the data have been received, the coloring inks are printed on the substrate in step 33.

The printer driver may comprise a menu for selecting the cosmetic ink cartridges to be used among other cartridges installed in the printer and/or the nature of the substrate that is printed. As a variant, the printer automatically recognizes that the cartridges to be used comprise cosmetic inks and adjusts the operating parameters accordingly. The cartridges may thus comprise an identifier, for example an electronic chip, for providing the printer with information relating to the nature of the coloring inks that they contain, in particular that said inks are of a cosmetic nature.

In one exemplary embodiment, the printer is configured to prohibit printing if the presence of a cartridge comprising a composition not intended to be placed in contact with human keratin materials, in particular the skin, the nails or the lips, is detected.

As a variant, the printer may perform printing even if the presence of a cartridge comprising a composition not intended to be brought into contact with human keratin materials, in particular the skin, the nails or the lips, is detected, this non-cosmetic ink cartridge possibly being used for printing on the substrate a piece of information relating to at least one of the cosmetic coloring inks borne by the substrate and/or to the nature of the keratin materials to be made up.

The printing of the substrate may take place in several passes, to make successive deposits of ink at the same place, so as to increase the amount of ink deposited on the substrate. The substrate may effect, for example, between 1 and 20 passes in the printer and the amount of cosmetic ink dry matter deposited ranges, for example, from 0.01 mg/cm$^2$ to 100 mg/cm$^2$, or even from 0.1 mg/cm$^2$ to 10 mg/cm$^2$, better still from 0.2 mg/cm$^2$ to 10 mg/cm$^2$, in particular from 0.2 mg/cm$^2$ to 5 mg/cm$^2$.

The printer may be arranged for detecting whether the ink previously deposited on the substrate is sufficiently dry before printing a new layer of ink, for example by measuring the electrical conduction between two points. The printer and/or the printer driver may be produced so as to inform the user of the need to wait a predefined period of time before performing further printing on the already-printed substrate. The printer and/or the driver may automatically suspend the printing of an already-printed substrate if sufficient time has not passed to allow sufficient drying. The printer is preferably arranged so as not to deliver the printed substrate as long as all the layers of ink to be printed have not been printed.

Figure 4:
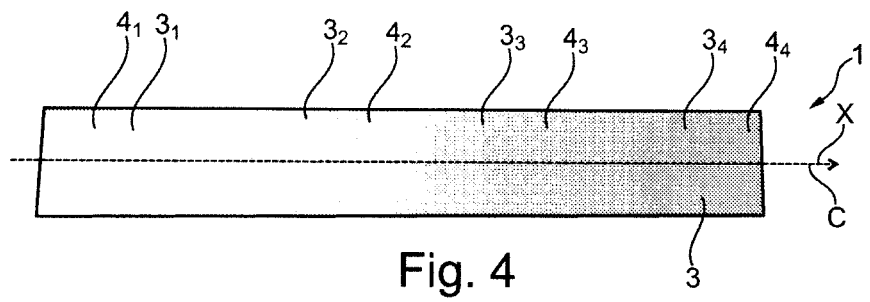

Represented in FIG. 4 is a variant of a device 1 according to the invention wherein the layers of coloring inks $4_1, \ldots, 4_4$ produce a color gradation along a path C connecting the regions $3_1, \ldots, 3_4$. The path C may, as illustrated, be linear. If the path has another shape, this does not represent a departure from the scope of the present invention.

As illustrated in FIG. 4, the regions $3_1, \ldots, 3_4$ form a band which extends along a longitudinal axis X, in this case combined with the path C.

At least one colorimetric characteristic chosen from L, C*, h, a and b can continuously evolve between the various regions $3_1, \ldots, 3_4$. It is possible for there to be no visible demarcation between the various regions $3_1, \ldots, 3_4$, as illustrated.

Figure 5:
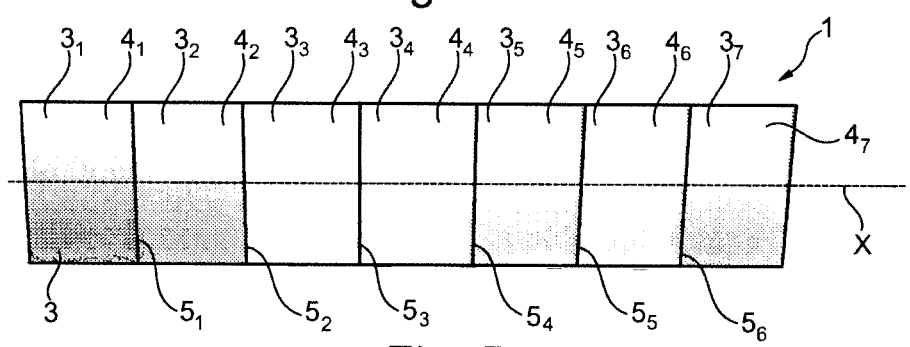

Represented in FIG. 5 is an implementation variant wherein the device 1 comprises a plurality of regions which follow one another along a longitudinal axis X. Each of the regions bears a layer of coloring ink producing a different flat color tint. The regions $3_1, \ldots, 3_7$ form, as in FIG. 4, a band. On the other hand, unlike FIG. 4, two successive regions exhibit between them a visible demarcation $5_1, \ldots, 5_6$.

Figure 6:
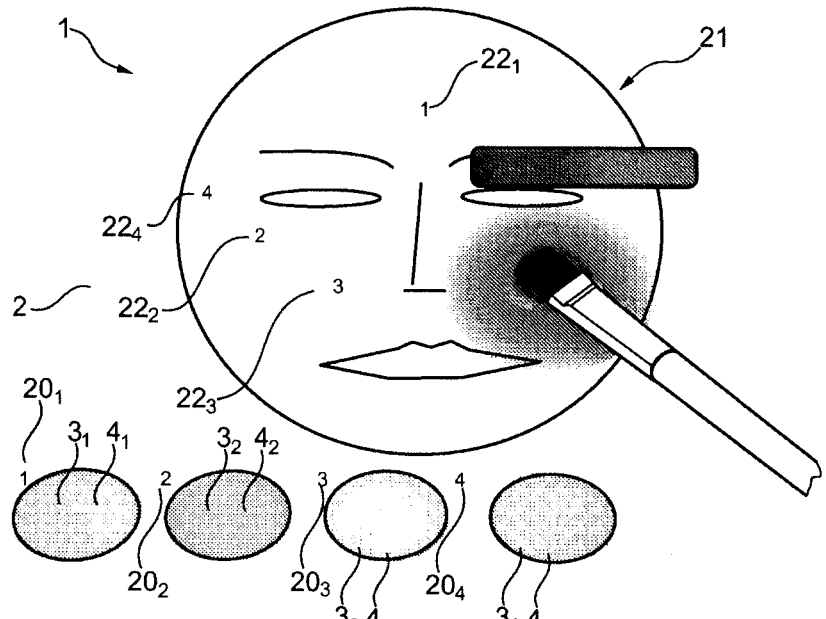

Represented in FIG. 6 is an example of a makeup device 1 according to the invention, wherein each of the regions $3_1, \ldots, 3_4$ is associated with an indicator $20_1, \ldots, 20_4$ borne by the substrate 2, making it possible to provide information on the location of the area of the keratin materials to which the coloring ink borne by this region is intended to be applied. The application can be carried out with a finger or with an applicator such as a roll, a brush, a fine brush, or a sponge, in particular made of synthetic foam.

The device 1 may, as illustrated, comprise a representation 21 of the area of the keratin materials to be made up, for example of the face in the example illustrated. This representation 21 can reveal the position to be made up with the various coloring inks by means of an apparent indication $22_1, \ldots, 22_4$, which may be identical to the indicator $20_1, \ldots, 20_4$.

The indicators $20_1, \ldots, 20_4$ may comprise alphanumeric and/or geometric symbols.

Represented in FIG. 7 is a device according to the invention, wherein the various layers of coloring inks $4_1, \ldots, 4_4$ produce visible optical effects that are different from one layer to the other and other than the color, for example that are of different brightness. The regions $3_i$ may be of the same color and may thus differ only by virtue of their brightness. As a variant, both the color and the brightness vary from one region to the other.

All or some of the coloring inks may each form a pattern as illustrated in FIG. 8. The patterns may be monochrome or polychrome. In this exemplary embodiment, all or some of the coloring inks may be applied by transfer. For example, the various regions $3_1, \ldots, 3_4$ are detachable from the rest of the substrate 2 and are configured to allow the application of the pattern by transfer by pressing the substrate onto the keratin materials to be made up.

Illustrated in FIG. 9 is a variant of a process according to the invention, wherein a layer of coloring ink 4 is exposed to the heat of a heating member 40 such that the layer of coloring ink 4 is fluidized or made more fluid after heating.

The layer of coloring ink thus reheated is then applied to the keratin materials to be made up, optionally after a period of time sufficient for the layer of coloring ink to lose, for example, at least 5° C., relative to the maximum temperature obtained from the heating, but still remains sufficiently hot.

In the variant illustrated in FIG. 10, a solvent such as water 51 is sprayed onto the layer of ink 4. Said layer is, for example, in solid form, and the solvent thus sprayed on allows it to be wetted. The ink may also not be solid, but the solvent that is sprayed on helps to make it more fluid. The coloring ink 4, once wetted, is then applied to the keratin materials. The solvent is sprayed, for example, using a pressurized container 50 of aerosol type, actuated by the user.

The process for preparing a device according to the invention may comprise, as illustrated in FIG. 11, a step 34 of simulating the appearance of the keratin materials coated with all or some of the coloring inks of the set chosen in step 31. The result of this simulation can be displayed on the screen of a machine, example on the same screen as that on which the coloring inks were proposed to the user, in step 31.

As a variant, a simulation of the appearance of the made-up keratin materials is provided at the same time as the set of coloring inks is proposed to the user and before the choice of the latter. At the end of the printing, information relating to the nature of the coloring inks selected can be recorded on a data storage medium, for example with a view to future reprinting.

Figure 12:
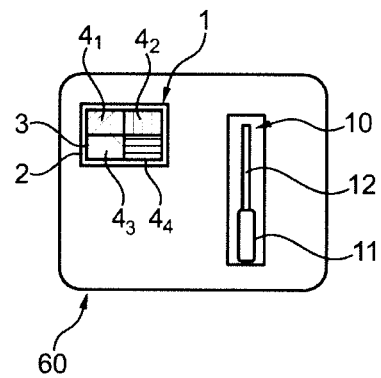
FIGS. 12 to 14 represent exemplary embodiments of cosmetic assemblies according to the invention.

Represented in FIG. 12 is an example of a cosmetic assembly 60 according to the invention. Said assembly comprises, in the same packaging, a makeup device 1 according to the invention, in the form of a palette bearing various layers of coloring inks $4_1, \ldots, 4_4$, and also an applicator 10 comprising a gripping part 12 and an applying part 11 intended to sample all or some of the coloring inks with a view to applying them to the keratin materials.

Figure 13:
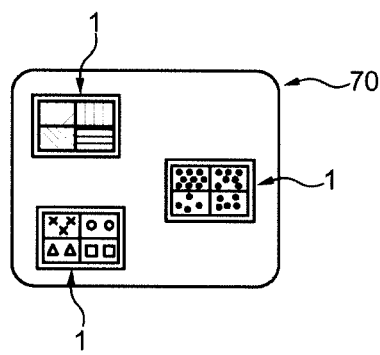

Represented in FIG. 13 is another example of a cosmetic assembly 70 according to the invention. Said assembly comprises, in the same packaging, a plurality of devices 1 according to the invention which each differ by virtue of the nature of the coloring inks that they bear. It is possible to have, in this packaging, devices 1 which differ by virtue of the nature of the keratin materials intended to receive the coloring inks that they bear. For example, a first device may comprise only coloring inks intended to be applied to the skin and a second device, different than the first, may comprise only coloring inks intended to be applied to the lips or the eyelashes.

Figure 14:
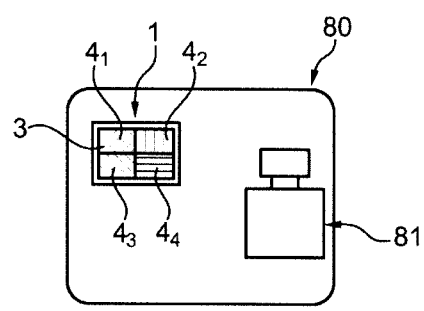

Represented in FIG. 14 is another exemplary embodiment of a cosmetic assembly 80 according to the invention. Said assembly comprises, in the same packaging, a device 1 according to the invention and also an additional cosmetic composition 81, in particular makeup composition, intended to be applied to the keratin materials in combination with all or some of the coloring inks.

In the examples of FIGS. 12 and 14, the packagings may be sealed closed, so as to prevent drying of the inks. The packagings may be made with means for avoiding contact of the inks with a surface other than the substrate, so as to reduce the risk of premature transfer. For example, the packaging comprises a thermoformed shell of which the wall extends at a distance from the areas of the substrate that are covered with inks.

Example

Four coloring inks corresponding to the formulations given in the table below were prepared:

TABLE 1

|  | Yellow I | Magenta I | Cyan I | Black I |
|---|---|---|---|---|
| Dye | D&C Yellow 8 1% | FD&C Red 4 1% | FD&C Blue 1 1% | (1) 1% |
| Ethylene glycol |  | 4% | 6% | 5% |
| Diethylene glycol | 8% |  |  |  |
| 1,5-Pentanediol |  | 4% | 4% |  |
| 2-Pyrrolidone | 5% | 5% | 4% |  |
| Glycerol | 8% | 3% | 4% | 7% |
| 2-Imidazolidinone | 4% | 4% | 4% | 9% |
| Water | 76% | 79% | 77% | 78% |
| Total | 100% | 100% | 100% | 100% |

(1) Brown-Replacement-J from Sensient

These compositions are introduced into Canon printing cartridges, then used with a Canon Prixma IP100 inkjet printer configured for printing a makeup palette comprising four regions, in the form of flat color tints each corresponding to a layer of just one ink. The printing is performed on a transparent plastic sheet for a commercial printer (smooth side), using each of the inks independently.

After each print, eight minutes are allowed to pass, and then all or some of the coloring inks deposited are sampled, in particular using a fine brush, so as to apply them to an area of skin, for example of the arm.

The expression "comprising a" should be understood to be synonymous with "comprising at least one". The expression "of between . . . and . . . " or "ranging from . . . to . . . " should be understood to include the limits.

The invention claimed is:

1. A cosmetic assembly comprising, in the same packaging, a makeup device comprising a substrate defining a printing surface having at least three regions printed with at least one layer of coloring ink, each region differing from one another at least by the color they produce after application to the keratin materials, for application to human keratin materials, said at least one coloring ink
    having been deposited by printing on the printing surface by at least one digital printer,
    not being covered with an adhesive, and
    producing, after application to the keratin materials, at least one visible optical effect among color and/or brightness, and
an applicator for the application of all or some of the coloring inks of the device to human keratin materials.

2. The cosmetic assembly, as claimed in claim 1, said at least one layer comprising one or more ink(s) intended to be applied to human keratin materials and capable of producing a makeup result by application to the keratin materials without addition of an intermediary fluid compound.

3. The cosmetic assembly as claimed in claim 1, at least two layers of coloring ink producing a gradation of the same optical effect, preferably the color, along a path connecting the regions and/or said at least one region being associated with an indicator making it possible to provide information on the location of the area of the keratin materials to which the coloring ink of the layer borne by said at least one region is intended to be applied.

4. The cosmetic assembly as claimed in claim 1, the layer of coloring ink comprising an oily substance and/or the substrate being made of a non-absorbent material, preferably made of plastic.

5. The cosmetic assembly as claimed in claim 1, the layers of coloring ink located in the various regions differing at least by virtue of their color.

6. The cosmetic assembly as claimed in claim 1, at least one of the layers of coloring ink being printed so as to form a pattern reproducing an appearance of relief and/or color heterogeneities of the skin.

7. The cosmetic assembly as claimed in claim 1, the printing of said at least one layer being carried out by four-color printing or with more than four inks of different colors.

8. The cosmetic assembly as claimed in claim 1, the ink being aqueous.

9. The cosmetic assembly as claimed in claim 1, the ink being pulverulent.

10. A process for preparing a cosmetic assembly as claimed in claim 1, comprising the step consisting in printing, using at least one printer, at least one layer of cosmetic coloring ink on at least one region of a printing surface of a substrate.

11. The process as claimed in claim 10, the printer being an inkjet printer or a laser printer.

12. The process as claimed in claim 10, comprising, before printing, a step of simulating the appearance of the keratin materials coated with one or more of the coloring inks to be printed, the simulation of the appearance of the keratin materials coated being displayed on a screen of a machine.

13. The process as claimed in claim 10, comprising a step of recording, on a data storage medium, information relating to the device prepared.

14. The process as claimed in claim 10, the choice of the coloring ink of said layer being made according to information relating to the appearance of the keratin materials to be made up.

15. The process as claimed in claim 10, comprising a step of recovering information relating to the nature of the layer of coloring ink stored on a computer medium, the printing being carried out according to this information.

16. A process for making up human keratin materials, comprising the step consisting in applying all or some of at least one coloring ink present on a cosmetic assembly as claimed in claim 1 to the human keratin materials.

17. The process as claimed in claim 16, a plurality of coloring inks of the makeup device being mixed before application to the keratin materials and all or some of the mixture being applied to the keratin materials.

18. The process as claimed in claim 16, also comprising a step of applying an additional cosmetic composition, different than the coloring inks present on the makeup device.

19. The process as claimed in claim 16, the coloring ink taken from a first layer being applied to a first area of the keratin materials and the coloring ink taken from a second layer, different than the first, being applied to a second area of the keratin materials, different than the first.

20. The process as claimed in claim 16, the application of the coloring ink(s) to the keratin materials being carried out without bringing the coloring ink(s) into contact with an intermediary fluid compound.

21. A process for preparing a makeup device comprising a substrate defining a printing surface having at least three regions each printed in a different color with at least one layer of coloring ink for application to human keratin materials, each coloring ink
- having been deposited by printing on the printing surface by at least one printer,
- not being covered with an adhesive, and
- producing, after application to the keratin materials, at least one visible optical effect among color and/or brightness, said at least one printer performing a first round of printing making it possible to obtain a first fraction of the layer of coloring ink and then at least one second round of printing making it possible to obtain a second fraction of the layer of coloring ink superposed on the first fraction.

22. A process for making up human keratin materials, comprising the step consisting in applying all or some of at least one coloring ink present on a makeup device comprising a substrate defining a printing surface having at least three regions each printed in a different color with at least one layer of coloring ink for application to human keratin materials, each coloring ink
- having been deposited by printing on the printing surface by at least one printer,
- not being covered with an adhesive, and
- producing, alter application to the keratin materials, at least one visible optical effect among color and/or brightness, the coloring ink being taken from the makeup device using an applicator and being applied to the keratin materials using said applicator.

* * * * *